(12) United States Patent
Tsuji et al.

(10) Patent No.: US 6,310,225 B1
(45) Date of Patent: Oct. 30, 2001

(54) PROCESSES FOR THE PREPARATION OF STEROID DERIVATIVES, INTERMEDIATES THEREFOR AND PROCESSES FOR THE PREPARATION OF THE INTERMEDIATES

(75) Inventors: Yoshihisa Tsuji; Toshimichi Mitani, both of Kurashiki (JP)

(73) Assignee: Kuraray Co., Ltd., Kurashiki (JP)

( * ) Notice: Subject to any disclaimer, the term of this patent is extended or adjusted under 35 U.S.C. 154(b) by 5 days.

(21) Appl. No.: 09/700,792

(22) PCT Filed: Mar. 14, 2000

(86) PCT No.: PCT/JP00/01535

§ 371 Date: Nov. 20, 2000

§ 102(e) Date: Nov. 20, 2000

(87) PCT Pub. No.: WO00/56759

PCT Pub. Date: Sep. 28, 2000

(30) Foreign Application Priority Data

Mar. 19, 1999 (JP) .................................................. 11-075490

(51) Int. Cl.$^7$ .................................. C07J 5/00; C07J 9/00; C07J 71/00

(52) U.S. Cl. ........................... 552/547; 552/583; 552/606; 552/608; 540/51

(58) Field of Search .............................. 540/51; 552/547, 552/583, 606, 608

*Primary Examiner*—Barbara P. Badio
(74) *Attorney, Agent, or Firm*—Oblon, Spivak, McClelland, Maier & Neustadt, P.C.

(57) ABSTRACT

Steroid derivatives useful as intermediates for producing vitamin D derivates as well as processes for producing the steroid derivatives are provided. The steroid derivatives include halide compounds represented by the following formulae:

wherein X, $R^1$ and $R^2$ are as defined by the specification.

14 Claims, No Drawings

US 6,310,225 B1

PROCESSES FOR THE PREPARATION OF STEROID DERIVATIVES, INTERMEDIATES THEREFOR AND PROCESSES FOR THE PREPARATION OF THE INTERMEDIATES

This application is a 371 of PCT/JP00/01535 filed Mar. 14, 2000.

TECHNICAL FIELD

The present invention relates to a process for producing steroid derivatives, intermediates thereof and processes for producing the intermediates. The steroid derivatives provided by the present invention are useful as intermediates for the synthesis of vitamin D derivatives, such as 1α,25-dihydroxyvitamin $D_3$ and 2β-(3-hydroxypropoxy)-1α,25-dihydroxyvitamin $D_3$, which have calcium metabolism modulating activity and differentiation inducing activity and are useful as therapeutic agents for diseases caused by calcium metabolism disorder, such as osteoporosis and osteomalacia, or as antitumor agents.

BACKGROUND ART

Known as the processes for producing vitamin D derivatives, such as 1α,25-dihydroxyvitamin $D_3$ and 2β-(3-hydroxypropoxy)-1α,25-dihydroxyvitamin $D_3$, and intermediates for the synthesis thereof are, among others, (1) the process for producing pregnane derivatives which comprises epoxidizing 21-hydroxy-20 -methyl-pregna-1,4,6-trien-3-one and reductively cleaving the resulting 1,2-epoxide (cf. JP Kokoku S62-14558), (2) the process for producing 1α,25-dihydroxy-7-dehydrocholesterol which comprises oxidizing 25-hydroxycholesterol with 2,3-dichloro-5,6-dicyano-1,4-benzoquinone (DDQ), protecting the hydroxy group at position 25 of the thus-obtained 25-hydroxycholesta-1,4,6-trien-3-one, enol-acetylating the position 3 of the protected compound and reducing the resulting compound (cf. U.S. Pat. No. 4,287,129), (3) the process for producing pregnane derivatives which comprises reducing 1α,2α-epoxy-20-methyl-4,6-pregnadien-3-on-21-ol at the position 3 thereof, then converting the resulting compound to the corresponding diepoxy alcohol by 4,5-epoxidization, oxidizing the hydroxy group at position 3 of the diepoxy alcohol, then reducing the oxidation product for simultaneous steric inversion, cleaving by reduction the epoxy moieties of the resulting compound, causing the resulting hydroxy group to rearrange and then eliminating it to thereby construct the 5,7-diene structure (cf. JP 2,731,543), (4) the process for producing steroid derivatives which comprises protecting the hydroxy group at position 22 or 24 of 22-hydroxy-23,24-dinorchola-1,4,6-trien-3-one or 24-hydroxy-chola-1,4,6-trien-3-one, then enol-acetylating the protected compound at position 3 and reducing the resulting compound (cf. JP 2,750,175) and (5) the process for producing 2β-(3-hydroxypropoxy)-1α,25-dihydroxyvitamin $D_3$ which comprises using the steroid derivative obtained by the method described in Japanese Patent Specification No. 2,750,175 (cf. JP Kokai H07-112998). Among these, the process (2) uses a starting material having the side chain skeleton. On the other hand, the processes (1), (3), (4) and (5) use starting materials with a functional group introduced therein at position 22 and introduce the side chain after modifying the ring A and ring B moieties.

As mentioned above, several processes for producing vitamin D derivatives, such as 1α,25-dihydroxyvitamin $D_3$ and 2β-(3-hydroxypropoxy)-1α,25-dihydroxyvitamin $D_3$, and intermediates for the synthesis thereof are already known.

However, no example is known of the production of vitamin D derivatives using a starting material having a halogen atom, which is a reactive substituent, as the functional group at position 22 and carrying out side chain introduction after modification of the ring A and ring B moieties.

On the other hand, an example of the synthesis of 7,8-didehydrodemosterol has been reported (cf. Schoenauer et al., Liebigs Ann. Chem., vol. 6, pages 1031–1042 (1983)). In that example, a complicated process was used; namely a steroid derivative having a chlorine atom at position 22 was used as the starting material, the ring A and ring B moieties were first modified, then the chlorine atom at position 22 was converted to an acetoxy group by treatment with tetrabutylammonium acetate, then a tosylate compound was derived from the acetoxy compound by hydrolysis and tosylation, the thus-obtained tosylate compound was converted to the corresponding aldehyde by Pfitzner-Moffat oxidation and then the side chain was introduced utilizing the Wittig reaction. Further, a steroid derivative having a chlorine atom at position 22 was used as the starting material and, after modification of the ring A and ring B moieties, the chlorine atom was converted to a more reactive iodine atom and an attempt was made, but unsuccessfully, to directly introduce the side chain basic skeleton of 7,8-didehydrodemosterol into the iodide by reacting with prenyl bromide-π-allylnickel complex.

Thus, it is an object of the present invention to provide steroid derivatives useful as intermediates for the production of vitamin D derivatives, such as 1α,25-dihydroxyvitamin $D_3$ and 2β-(3-hydroxypropoxy)-1α,25-dihydroxyvitamin $D_3$, and a process for producing the steroid derivatives.

Intensive investigations made by the present inventors with the expectation that if it becomes possible to introduce various side chains into a steroid derivative having a halogen atom at position 22, which is used as the starting material, by utilizing the reactivity of that moiety, the complicated reaction steps for protection and deprotection required for protecting such a functional group as a hydroxy group prior to modification of the ring A and ring B moieties will become unnecessary, hence it will become possible to produce various vitamin D derivatives as well as intermediates for the synthesis thereof by a simplified process as compared with the prior art processes for producing vitamin D derivatives and intermediates for the synthesis thereof which comprise side chain introduction following modification of the ring A and ring B moieties, have now led to the present invention.

DISCLOSURE OF INVENTION

According to the present invention, the above object can be accomplished by providing:

(1) A halide compound represented by the general formula (II) (hereinafter referred to as "halide compound(II)" for short):

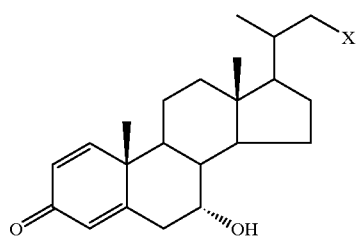

(II)

wherein X represents a bromine atom or an iodine atom;

(2) A 1,4,6-trien-3-one compound represented by the general formula (III) (hereinafter referred to as "1,4,6-trien-3-one compound (III)" for short):

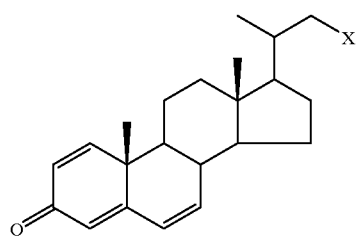

(III)

wherein X is as defined above;

(3) A 1,3,5,7-tetraene compound represented by the general formula (IV) (hereinafter referred to as "1,3,5,7-tetraene compound (IV)" for short):

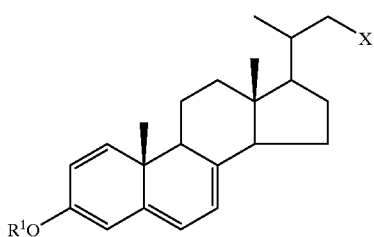

(IV)

wherein X is as defined above and $R^1$ represents an acyl group;

(4) A 1,5,7-triene compound represented by the general formula (V):

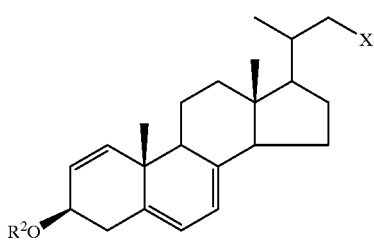

(V)

wherein X is as defined above and $R^2$ represents a hydrogen atom or a hydroxy-protecting group;

(5) A process for producing 3β-hydroxy-1,5,7-triene compounds represented by the general formula (V-1) (hereinafter referred to as "3β-hydroxy-1,5,7-triene compounds (V-1)" for short):

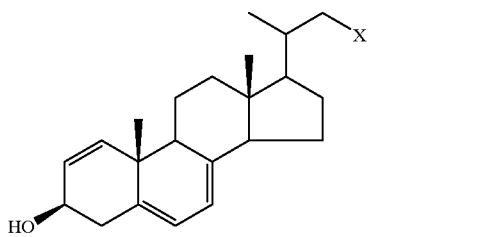

(V-1)

wherein X is as defined above, which comprises reducing a 1,3,5,7-tetraene compound (IV);

(6) A process for producing 1,3,5,7-tetraene compounds (IV) which comprises subjecting a 1,4,6-trien-3-one compound (III) to enol esterification;

(7) A process for producing 1,4,6-trien-3-one compounds (III) which comprises dehydrating the hydroxy group at position 7 of a halide compound (II);

(8) A process for producing halide compounds (II) which comprises reacting a sulfonate compound represented by the general formula (I) (hereinafter referred to as "sulfonate compound (I)" for short):

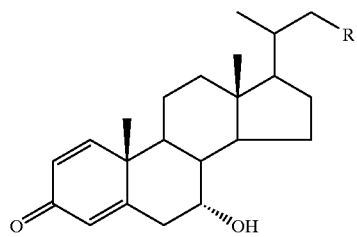

(I)

wherein R represents an organic sulfonyloxy group, with a brominating agent or an iodinating agent;

(9) A process for producing diene adducts represented by the general formula (X) (hereinafter referred to as "diene adducts (X)" for short):

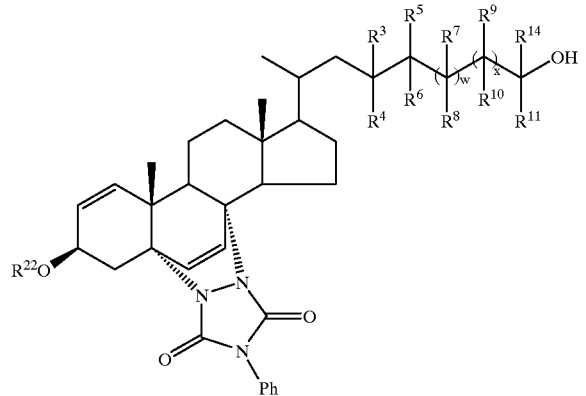

(X)

wherein $R^{22}$ represents a hydroxy-protecting group, $R^3$, $R^4$, $R^5$ and $R^6$ each represents a hydrogen atom or an alkyl group, $R^7$, $R^8$, $R^9$ and $R^{10}$ each represents a hydrogen atom, a fluorine atom, a protected hydroxy group or an alkyl group, $R^3$ and $R^5$, $R^4$ and $R^6$ or $R^5$ and $R^7$ may combinedly represent a single bond, $R^{11}$ represents a hydrogen atom, a trifluoromethyl group, a cycloalkyl group or an alkyl group which may optionally be substituted by a protected hydroxy group, $R^{14}$ represents an alkyl group, w represents 0 or 1 and x represents 0, 1 or 2, which comprises reacting a sulfonate compound (I) with a brominating agent or an iodinating agent, to give a halide compound (II), dehydrating the hydroxy group at position 7 of the thus-obtained halide compound (II) to give a 1,4,6-trien-3-one compound (III), subjecting the thus-obtained 1,4,6-trien-3-one compound (III) to enol esterification to give a 1,3,5,7-tetraene compound (IV), reducing the thus-obtained 1,3,5,7-tetraene compound (IV) to give a 3β-hydroxy-1,5,7-triene compound (V-1), protecting the hydroxy group at position 3 of the thus-obtained 3β-hydroxy-1,5,7-triene compound (V-1) to give a 1,5,7-triene compound represented by the general formula (V-2) (hereinafter referred to as "1,5,7-triene compound (V-2)" for short):

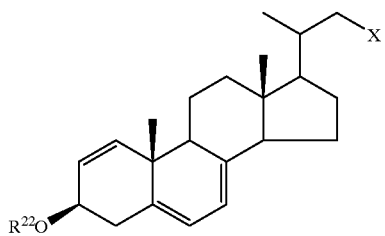

(V-2)

wherein X is as defined above and $R^{22}$ represents a hydroxy-protecting group, reacting the thus-obtained 1,5,7-triene compound (V-2) with an organometallic compound represented by the general formula (VI) (hereinafter referred to as "organometallic compound (VI)" for short):

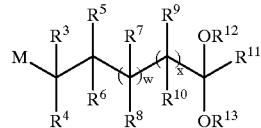

(VI)

wherein $R^3$, $R^4$, $R^5$, $R^6$, $R^7$, $R^8$, $R^9$, $R^{10}$, $R^{11}$, w and x are as defined above, $R^{12}$ and $R^{13}$ each independently represents an alkyl group or combinedly represent an alkylene group which may optionally be substituted by an alkyl group or groups and M represents Li or MgY (in which Y represents a halogen atom), in the presence of a copper compound to give an acetal compound represented by the general formula (VII) (hereinafter referred to as "acetal compound (VII)" for short):

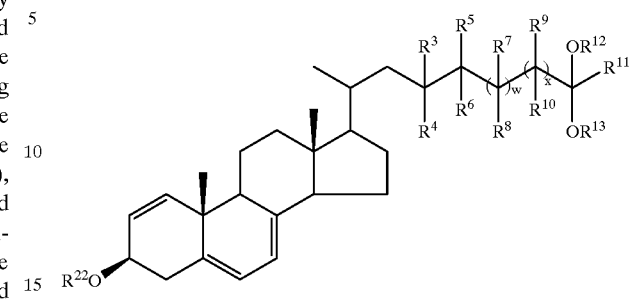

(VII)

wherein $R^{22}$, $R^3$, $R^4$, $R^5$, $R^6$, $R^7$, $R^8$, $R^9$, $R^{10}$, $R^{11}$, $R^{12}$, $R^{13}$, w and x are as defined above, deprotecting the acetal moiety of the thus-obtained acetal compound (VII) to give a ketone compound represented by the general formula (VIII) (hereinafter referred to as "ketone compound (VIII)" for short):

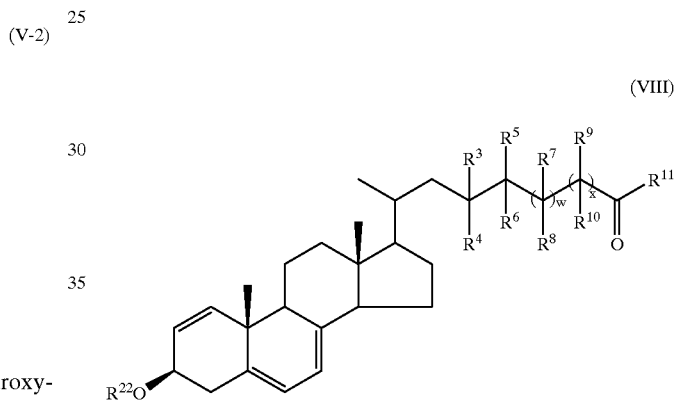

(VIII)

wherein $R^{22}$, $R^3$, $R^4$, $R^5$, $R^6$, $R^7$, $R^8$, $R^9$, $R^{10}$, $R^{11}$, w and x are as defined above, reacting the thus-obtained ketone compound (VIII) with an alkylating agent to give a hydroxy compound represented by the general formula (IX) (hereinafter referred to as "hydroxy compound (IX)" for short):

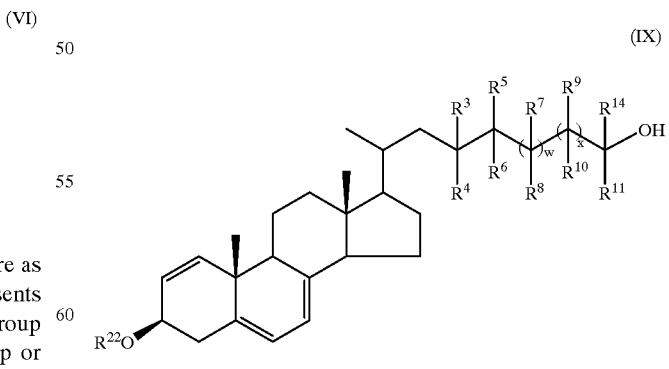

(IX)

wherein $R^{22}$, $R^3$, $R^4$, $R^5$, $R^6$, $R^7$, $R^8$, $R^9$, $R^{10}$, $R^{11}$, $R^{14}$, w and x are as defined above, and reacting the thus-obtained hydroxy compound (IX) with 4-phenyl-1,2,4-triazoline-3,5-dione;

(10) A process for producing diene adducts (X) which comprises reacting a ketone compound (VIII) with an alkylating agent to give a hydroxy compound (IX) and reacting the thus-obtained hydroxy compound (IX) with 4-phenyl-1,2,4-triazoline-3,5-dione;

(11) A process for producing hydroxy compounds (IX) which comprises reacting a ketone compound (VIII) with an alkylating agent;

(12) A process for producing ketone compounds (VIII) which comprises reacting a 1,5,7-triene compound (V-2) with an organometallic compound (VI) in the presence of a copper compound to give an acetal compound (VII) and deprotecting the acetal moiety of the thus-obtained acetal compound (VII);

(13) A process for producing acetal compounds (VII) which comprises reacting a 1,5,7-triene compound (V-2) with an organometallic compound (VI) in the presence of a copper compound; and

(14) A process for producing 1,5,7-triene compounds (V-2) which comprises reacting a sulfonate compound (I) with a brominating agent or an iodinating agent to give a halide compound (II), dehydrating the hydroxy group at position 7 of the resulting halide compound (II) to give a 1,4,6-trien-3-one compound (III), subjecting the thus-obtained 1,4,6-trien-3-one compound (III) to enol esterification to give a 1,3,5,7-tetraene compound (IV), reducing the thus-obtained 1,3,5,7-tetraene compound (IV) to give a 3β-hydroxy-1,5,7-triene compound (V-1) and protecting the hydroxy group at position 3 of the thus-obtained 3β-hydroxy-1,5,7-triene compound (V-1).

BEST MODES FOR CARRYING OUT THE INVENTION

The organic sulfonyloxy group represented by R includes methanesulfonyloxy, ethanesulfonyloxy, benzenesulfonyloxy, toluenesulfonyloxy, benzylsulfonyloxy and the like.

The halogen atom represented by Y includes a chlorine atom, a bromine atom, an iodine atom, etc.

The acyl group represented by $R^1$ includes acetyl, trichloroacetyl, trifluoroacetyl and the like.

The hydroxy-protecting group represented by each of $R^2$ and $R^{22}$ may be any protecting group known in the art as a hydroxy-protecting group, without any particular restriction, and includes, among others, trisubstituted silyl groups such as trimethylsilyl, triethylsilyl, triisopropylsilyl, tert-butyldimethylsilyl and tert-butyldiphenylsilyl; 1-(alkoxy) alkyl groups such as methoxymethyl, methoxyethoxymethyl and 1-ethoxyethyl; 2-oxacycloalkyl groups such as tetrahydrofuranyl and tetrahydropyranyl; alkyl groups such as tert-butyl; aralkyl groups such as benzyl and p-methoxybenzyl; aryl groups such as p-methoxyphenyl; acyl groups such as acetyl, trifluoroacetyl, benzoyl and pivaloyl; and alkoxycarbonyl groups such as methoxycarbonyl, ethoxycarbonyl and allyloxycarbonyl.

The protected hydroxy group represented by each of $R^7$, $R^8$, $R^9$ and $R^{10}$ includes protected hydroxy groups whose protective group is a hydroxy-protecting group represented by $R^2$ and $R^{22}$.

The alkyl group represented by $R^3$, $R^4$, $R^5$, $R^6$, $R^7$, $R^8$, $R^9$, $R^{10}$, $R^{12}$, $R^{13}$ and $R^{14}$ includes methyl, ethyl, propyl, isopropyl, butyl, isobutyl, pentyl, hexyl and the like.

The alkyl group represented by $R^{11}$ includes methyl, ethyl, propyl, isopropyl, butyl, isobutyl, pentyl, hexyl and the like. These alkyl groups may be substituted by a protected hydroxy group whose protective group is a hydroxy-protecting group represented by $R^2$ or $R^{22}$.

The cycloalkyl group represented by $R^{11}$ includes, among others, cyclopropyl, cyclobutyl, cyclopentyl and cyclohexyl.

The alkylene group, which may optionally be substituted by an alkyl group or groups, as represented combinedly by $R^{12}$ and $R^{13}$ includes ethylene, methylethylene, 1,1-dimethylethylene, 1,2-dimethylethylene, trimethylene, 1-methyltrimethylene, 2-methyltrimethylene, 2,2-dimethyltrimethylene, 1,3-dimethyltrimethylene, etc.

In the following, the respective steps are described.

Step 1: Production of halide compounds (II) by reacting a sulfonate compound (I) with a brominating agent or an iodinating agent As the brominating or iodinating agent, there may be mentioned, for example, alkali metal bromides or alkali metal iodides such as sodium bromide, potassium bromide, lithium bromide, sodium iodide, potassium iodide and lithium iodide. The brominating or iodinating agent is preferably used in an amount within the range of 1 to 10 moles per mole of the sulfonate compound (I).

The reaction is preferably carried out in the presence of a solvent. The solvent to be used is not particularly restricted unless the reaction is adversely affected. Thus, there may be mentioned, for example, ketones such as acetone and methyl ethyl ketone: ethers such as diethyl ether, diisopropyl ether and tetrahydrofuran; alcohols such as methanol and ethanol; and amides such as dimethylformamide. The solvent is preferably used in an amount of 5 to 200 parts by weight per part by weight of the sulfonate compound (I).

The reaction temperature is preferably within the range of 0 to 100° C. The reaction time is generally within the range of 1 to 10 hours.

Preferably, the reaction is carried out by mixing and dissolving the sulfonate compound (I) in the solvent, adding the brominating or iodinating agent to the solution and stirring the mixture at a predetermined temperature.

The thus-obtained halide compound (II) can be isolated and purified from the reaction mixture by the same isolation and/or purification techniques as commonly used in organic reactions in general. For example, the reaction mixture is filtered to thereby remove the insoluble matter, the filtrate is concentrated and the crude product thus obtained is purified, for example by recrystallization or chromatography.

Step 2: Production of 1,4,6-trien-3-one compounds (III) by dehydrating the hydroxy group at position 7 of the halide compound (II).

The reaction is preferably carried out in the presence of a basic substance or an acidic substance. Usable as the basic substance are sodium hydroxide, potassium hydroxide and the like. It is generally preferred that the basic substance be used in an amount within the range of 1 to 10 moles per mole of the halide compound (II), although this range is not critical. Usable as the acidic substance are sulfonic acids such as p-toluenesulfonic acid and methanesufonic acid; inorganic acids such as hydrochloric acid and sulfuric acid; and so forth. It is generally preferred that the acidic substance be used in an amount within the range of 0.1 to 10 moles per mole of the halide compound (II), although this range is not critical.

The reaction is preferably carried out in the presence of a solvent. Those solvents which will not adversely affect the reaction may be used as the solvent, without any particular restriction, including aliphatic or aromatic hydrocarbons such as hexane, heptane, cyclohexane, benzene, toluene and xylene; ketones such as acetone and methyl ethyl ketone; esters such as ethyl acetate, butyl acetate and isopropyl acetate; ethers such as diethyl ether, diisopropyl ether and tetrahydrofuran; and halogenated hydrocarbons such as methylene chloride and chloroform. The solvent is preferably used in an amount within the range of 5 to 200 parts by weight per part by weight of the halide compound (II).

The reaction temperature is preferably within the range of 0 to 200° C. The reaction time is generally within the range of 3 to 12 hours.

The reaction is preferably carried out by mixing the acidic or basic substance, the solvent and the halide compound (II) and stirring the resulting mixture at a predetermined temperature. As the reaction proceeds, water is formed, and the reaction is preferably allowed to proceed while removing the water, whereby the 1,4,6-trien-3-one compound (III) can be obtained in a high yield. While the method of removing water is not particularly restricted, the water removal can efficiently be carried out by using a solvent capable of forming an azeotrope with water and distilling off the water by azeotropic distillation with the solvent. It is also possible to allow a dehydrating agent which will not adversely affect the reaction, for example molecular sieves, to coexist in the system.

The thus-obtained 1,4,6-trien-3-one compound (III) can be isolated and purified from the reaction mixture by the same isolation and/or purification techniques as commonly used in organic reactions in general. For example, the reaction mixture is filtered, the filtrate is concentrated and the crude product thus obtained is purified, for example by recrystallization or chromatography.

Step 3: Production of 1,3,5,7-tetraene compounds (IV) by subjecting a 1,4,6-trien-3-one compound (III) to enol esterification For the enol esterification reaction, use may be made, as the acylating agent, of acid anhydrides such as acetic anhydride, trifluoroacetic anhydride and trichloroacetic anhydride; acid halides such as acetyl chloride, trifluoroacetyl chloride and trichloroacetyl chloride; and esters such as isopropenyl acetate, isopropenyl trifluoroacetate and isopropenyl trichloroacetate. The acylating agent is preferably used in an amount within the range of 1 to 100 moles per mole of the 1,4,6-trien-3-one compound (III).

The reaction may be carried out in the presence or absence of a solvent. The solvent to be used is not particularly restricted unless the reaction is adversely affected. Thus, mention may be made of aliphatic or aromatic hydrocarbons such as hexane, heptane, cyclohexane, benzene, toluene and xylene; and esters such as ethyl acetate, butyl acetate and isopropyl acetate, for instance. It is also possible to use the above-mentioned acylating agent itself as the solvent. In cases where a solvent is used, it is preferably used in an amount within the range of 5 to 200 parts by weight per part by weight of the 1,4,6-trien-3-one compound (III).

The reaction may also be carried out in the presence of a basic substance or an acidic substance. As specific examples of the basic substance, there may be mentioned aromatic or aliphatic amines such as pyridine, triethylamine and diisopropylethylamine. In cases where a basic substance is allowed to coexist, it is preferably used in an amount within the range of 1 to 20 moles per mole of the 1,4,6-trien-3-one compound (III). As specific examples of the acidic substance, there may be mentioned sulfonic acids such as p-toluenesulfonic acid and methanesulfonic acid; and inorganic acids such as hydrochloric acid and sulfuric acid, among others. In cases where an acidic substance is allowed to coexist, it is preferably used in an amount within the range of 0.1 to 10 moles per mole of the 1,4,6-trien-3-one compound (III).

The reaction temperature is preferably within the range of 0 to 200° C., more preferably within the range of 80 to 150° C. The reaction time is generally within the range of 3 to 12 hours.

The reaction is preferably carried out by mixing the 1,4,6-trien-3-one compound (III) with the solvent and acylating agent adding the basic substance or acidic substance, if necessary, and stirring the mixture at a predetermined temperature.

The thus-obtained 1,3,5,7-tetraene compound (IV) can be isolated and purified from the reaction mixture by the same isolation and/or purification techniques as commonly used in organic reactions in general. For example, the reaction mixture is poured into an aqueous solution of sodium hydrogen carbonate, the mixture is extracted with an organic solvent such as ethyl acetate, the extract is washed in sequence with an aqueous solution of sodium hydrogen carbonate and an aqueous solution of sodium chloride, then dried over anhydrous sodium sulfate or the like and concentrated, and the crude product thus obtained is purified by recrystallization or chromatography, for instance.

Step 4: Production of 3β-hydroxy-1,5,7-triene compounds (V-1) by reducing a 1,3,5,7-tetraene compound (IV)

As the reducing agent, there may be mentioned sodium borohydride, calcium borohydride, lithium borohydride and zinc borohydride. Among them, calcium borohydride is preferred. The reducing agent is preferably used in an amount of 1 to 10 moles per mole of the 1,3,5,7-tetraene compound (IV).

The reaction is preferably carried out in the presence of a solvent. The solvent to be used depends on the reducing agent employed. Preferred are, however, alcohols such as methanol and ethanol; and ethers such as diethyl ether, tetrahydrofuran and dimethoxyethane. The solvent is preferably used in an amount of 5 to 200 parts by weight per part by weight of the 1,3,5,7-tetraene compound (IV).

The reaction temperature is preferably within the range of −70 to +100° C., more preferably within the range of −10 to +30° C. The reaction time is generally within the range of 3 to 12 hours.

The reaction is preferably carried out by mixing the 1,3,5,7-tetraene compound (IV) with the solvent, adjusting the temperature to a predetermined level, and adding the reducing agent to the solution.

The thus-obtained 3β-hydroxy-1,5,7-triene compound (V-1) can be isolated and purified from the reaction mixture by the same isolation and/or purification techniques as commonly used in organic reactions in general. For example, the excess reducing agent is decomposed by adding water, an aqueous solution of sodium sulfate, dilute hydrochloric acid, an aqueous solution of acetic acid or methanol, for instance, to the reaction mixture and, after further dilution with water, if necessary, the mixture is extracted with an organic solvent such as ethyl acetate. The extract is washed in sequence with an aqueous solution of sodium hydrogen carbonate and an aqueous solution of sodium chloride, dried over anhydrous sodium sulfate or the like and concentrated, and the thus-obtained crude product is purified, for example, by recrystallization or chromatography.

Step 5: Production of 1,5,7-triene compounds (V-2) by protecting the hydroxy group at position 3 of a 3β-hydroxy-1,5,7-triene compound (V-1).

The hydroxy group at position 3 of the 3β-hydroxy-1,5,7-triene compound (V-1) can be protected in the same manner as in ordinary hydroxy group protection steps. In the production process according to the present invention, the use of bulky trisubstituted silyl groups such as tert-butyldimethylsilyl and tert-butyldiphenylsilyl as the hydroxy-protecting group is particularly preferred. When such a bulky trisubstituted silyl group is used as the protective group, the reaction can be carried out by bringing a trisubstituted silyl halide, such as tert-butyldimethylsilyl chloride or tert-butyldiphenylsilyl chloride or a trisubstituted silyl trifluoromethanesulfonate, such as tert-butyldimethylsilyl trifluoromethanesulfonate or tert-butyldiphenylsilyl trifluoromethanesulfonate, into contact with the 3β-hydroxy-1,5,7-triene compound (V-1) in the presence of a base such as imidazole or 2,6-lutidine.

The thus-obtained 1,5,7-triene compound (V-2) can be isolated and purified from the reaction mixture by the same isolation and/or purification techniques as commonly used in organic reactions in general. For example, the reaction mixture is poured into an aqueous solution of sodium hydrogen carbonate, the mixture is extracted with an organic solvent such as methylene chloride, the extract is washed in sequence with dilute hydrochloric acid, an aqueous solution of sodium hydrogen carbonate and an aqueous solution of sodium chloride, dried over anhydrous sodium sulfate or the like and then concentrated, and the thus-obtained crude product is purified by recrystallization or chromatography, for instance.

Step 6: Production of acetal compounds (VII) by reacting a 1,5,7-triene compound (V-2) with an organometallic compound (VI) in the presence of a copper compound.

As the copper compound, there may be mentioned, for example, cuprous bromide, cuprous bromide-dimethyl sulfide complex, cuprous iodide and cuprous cyanide. The copper compound is preferably used in an amount of 0.1 to 10 moles per mole of the 1,5,7-triene compound (V-2).

As specific examples of the organometallic compound (VI), there may be mentioned compounds represented by the following formulas:

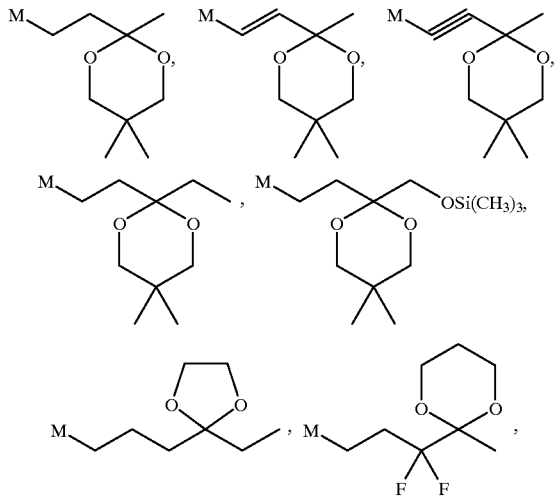

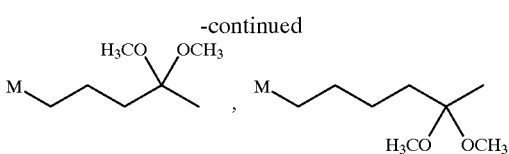

(In the above formulas, M is as defined above.)

When, among these, bromo[2-(2,5,5-trimethyl-1,3-dioxan-2-yl)ethyl]magnesium for instance, is used, intermediates for the synthesis of 1α,25-dihydroxyvitamin $D_3$ can be obtained.

The organometallic compound (VI) is preferably used in an amount of 1 to 10 moles per mole of the 1,5,7-triene compound (V-2).

The reaction is preferably carried out in the presence of a solvent. The solvent to be used is not particularly restricted unless the reaction is adversely affected. Thus, mention may be made of aliphatic or aromatic hydrocarbons such as hexane, heptane, cyclohexane, benzene, toluene and xylene; and ethers such as diethyl ether, diisopropyl ether and tetrahydrofuran, for instance. Among them, tetrahydrofuran is preferred. The solvent is preferably used in an amount within the range of 5 to 200 parts per part by weight of the 1,5,7-triene compound V-2).

The reaction temperature is preferably within the range of −70 to +100° C., more preferably within the range of −10 to +30° C. The reaction time is generally within the range of 1 to 72 hours.

The reaction is preferably carried out by suspending the copper compound in the solvent, adjusting the temperature to a predetermined level, adding a solution of the organometallic compound (VI) to that mixture and, then, adding, to this solution, a solution of the 1,5,7-triene compound (V-2) in the solvent.

The thus-obtained acetal compound (VII) can be isolated and purified from the reaction mixture by the same isolation and/or purification techniques as commonly used in organic reactions in general. For example, the reaction mixture is poured into a saturated aqueous solution of ammonium chloride, the mixture is extracted with an organic solvent such as ethyl acetate, the extract is washed in sequence with a saturated aqueous solution of ammonium chloride and an aqueous solution of sodium chloride, then dried over anhydrous sodium sulfate or the like and concentrated, and the thus-obtained crude product is purified by recrystallization or chromatography, for instance.

Step 7: Production of ketone compounds (VIII) by deprotecting the acetal moiety of an acetal compound (VII)

The deprotection of the acetal moiety of the acetal compound (VII) can be effected in the same manner as in deprotecting acetal moieties in general. For example, it can be effected by treating the acetal compound (VII) with water or a carbonyl compound such as acetone or methyl ethyl ketone in a solvent, which will not adversely affect the reaction, in the presence of an acidic substance, for example an organic acid such as p-toluenesulfonic acid or methanesulfonic acid, or an inorganic acid such as dilute hydrochloric acid or dilute sulfuric acid.

The thus-obtained ketone compound (VIII) can be isolated and purified from the reaction mixture by the same isolation and/or purification techniques as commonly used in organic reactions in general. For example, the reaction mixture is concentrated under reduced pressure and the crude product obtained is purified by recrystallization or chromatography, for instance.

Step 8: Production of hydroxy compounds (IX) by reacting a ketone compound (VIII) with an alkylating agent As the alkylating agent, there may be mentioned alkyl-metal compounds such as methylmagnesium bromide, methylmagnesium chloride, ethylmagnesium bromide, ethylmagnesium chloride, propylmagnesium bromide, propylmagnesium chloride, butylmagnesium bromide, butylmagnesium chloride, isobutylmagnesium bromide, isobutylmagnesium chloride, sec-butylmagnesium bromide, sec-butylmagnesium chloride, tert-butylmagnesium bromide, tert-butylmagnesium chloride, methyllithium, ethyllithium, propyllithium, butyllithium, isobutyllithium, sec-butyllithium and tert-butyllithium. The alkylating agent is preferably used in an amount of 1 to 10 moles per mole of the ketone compound (VIII).

The reaction is preferably carried out in the presence of a solvent. The solvent to be used is not particularly restricted unless the reaction is adversely affected. Thus, mention may be made of aliphatic or aromatic hydrocarbons such as hexane, heptane, cyclohexane, benzene, toluene and xylene; and ethers such as diethyl ether, diisopropyl ether and tetrahydrofuran, for instance. Among them, tetrahydrofuran is preferred. The solvent is preferably used in an amount within the range of 5 to 200 parts per part by weight of the ketone compound (VIII).

The reaction temperature is preferably within the range of −70 to +100° C., more preferably within the range of −50 to 0° C. The reaction time is generally within the range of 1 to 10 hours.

The reaction is preferably carried out, for example, by adjusting the temperature of a solution of the alkylating agent to a predetermined level and adding thereto a solution of the ketone compound (VIII) in the solvent.

The thus-obtained hydroxy compound (IX) can be isolated and purified from the reaction mixture by the same isolation and/or purification techniques as commonly used in organic reactions in general. For example, the reaction mixture is poured into a saturated aqueous solution of ammonium chloride, the mixture is extracted with an organic solvent such as ethyl acetate, the extract is washed in sequence with an aqueous solution of sodium hydrogen carbonate and an aqueous solution of sodium chloride, then dried over anhydrous sodium sulfate or the like and concentrated, and the thus-obtained crude product is purified by recrystallization or chromatography, for instance.

Step 9: Production of diene adducts (X) by reacting a hydroxy compound (IX) with 4-phenyl-1,2,4-triazoline-3,5-dione 4-Phenyl-1,2,4-triazoline-3,5-dione is preferably used in an amount of 1 to 3 moles per mole of the hydroxy compound (IX).

The reaction is preferably carried out in the presence of a solvent. The solvent to be used is not particularly restricted unless the reaction is adversely affected. Thus, mention may be made of aliphatic or aromatic hydrocarbons such as hexane, heptane, cyclohexane, benzene, toluene and xylene; halogenated hydrocarbons such as methylene chloride and chloroform; ethers such as diethyl ether, diisopropyl ether and tetrahydrofuran; ketones such as acetone and methyl ethyl ketone; and esters such as ethyl acetate and butyl acetate, for instance. The solvent is preferably used in an amount within the range of about 5 to 200 parts per part by weight of the hydroxy compound (IX).

The reaction temperature is preferably within the range of −70 to +100° C., more preferably within the range of 0 to 30° C. The reaction time is generally within the range of about 1 to 5 hours.

The reaction is preferably carried out by mixing the hydroxy compound (IX) with the solvent and adding to this solution 4-phenyl-1,2,4-triazoline-3,5-dione as it is or in the form of a solution in the solvent.

The thus-obtained diene adduct (X) can be isolated and purified from the reaction mixture by the same isolation and/or purification techniques as commonly used in organic reactions in general. For example, the reaction mixture as such is concentrated and the thus-obtained crude product is purified by recrystallization or chromatography, for instance.

The diene adduct (X) can be converted, for example, to 2β-(3-hydroxypropoxy)-1α,25-dihydroxyvitamin D$_3$ by the process shown below under reaction scheme (1) (cf. N. Kubodera et al., Chem. Pharm. Bull., vol. 41, pages 1111–1113 (1993)).

Reaction scheme (1)

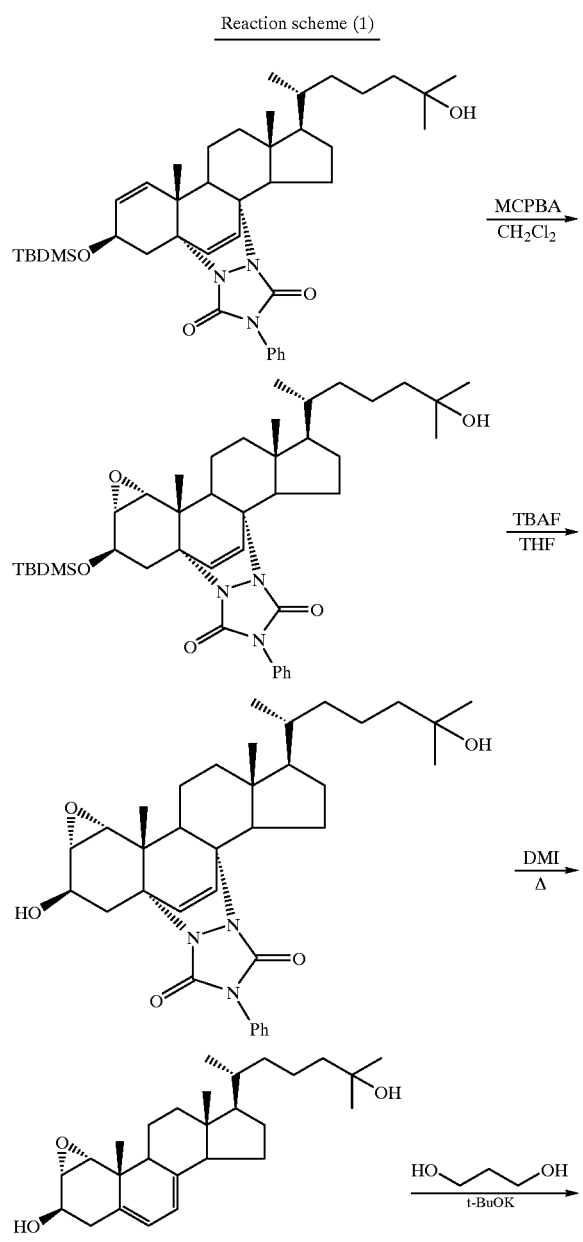

-continued

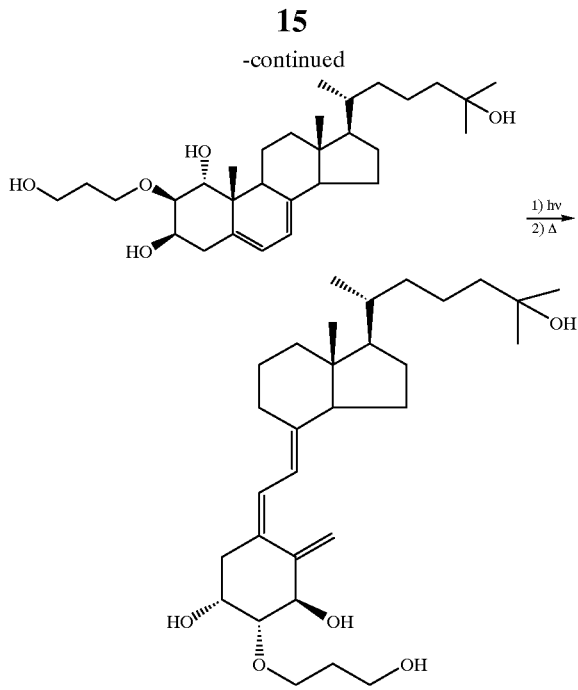

TBDMS = t-butyldimethylsilyl
TBAF = tetrabutylammonium fluoride
MCPBA = m-chloroperbenzoic acid
DMI = 1, 3-dimethyl-2-imidazolidinone The sulfonate compound (I) to be used as a starting material in the practice of the invention can be prepared by reducing (7α,20S)-7-hydroxy-3-oxo-pregna-1,4-diene-20-carbaldehyde or the 20-position epimer thereof and sulfonylating the resulting hydroxy group (cf. Reference Example 1 and Reference Example 2). (7α,20S)-7-Hydroxy-3-oxo-pregna-1,4-diene-20-carbaldehyde can be prepared by subjecting 3α,7α-dihydroxy-5,β-cholanic acid and/or a salt thereof to a conversion reaction using a microorganism (cf. JP 2,525,049).

The following examples illustrate the present invention more specifically. These examples, however, are by no means limitative of the scope of the invention.

Reference Example 1

Ethanol (200 ml) was added to 20.0 g of (7α,20S)-7-hydroxy-3-oxo-pregna-1,4-diene-20-carbaldehyde. To this solution was added 0.61 g of sodium borohydride in several portions with stirring under ice cooling. After completion of the addition, the mixture was further stirred for 1 hour under ice cooling. The reaction mixture was neutralized with 1 N hydrochloric acid, then 200 ml of water was added, and the ethanol was distilled off under reduced pressure. The precipitate was collected by filtration, washed with water, then dehydrated by adding toluene to the precipitate and removing water by azeotropic distillation, and concentrated to give 18.8 g of (7α,20S)-7,21-dihydroxy-20-methyl-pregna-1,4-dien-3-one (yield 93%).

$^1$H-NMR spectrum (270 MHz, CDCl$_3$, TMS, ppm) δ: 0.77 (s, 3H), 1.05 (d, J=6.6 Hz, 3H), 1.24 (s, 3H), 2.49 (dd, J=13.9, 3.3 Hz, 1H), 2.74 (ddd, J=13.9, 3.3 Hz, 1.8 Hz, 1H), 3.37 (dd, J=10.2, 6.9 Hz, 1H), 3.64 (dd, J=10.2, 3.3 Hz, 1H), 4.04 (br s, 1H), 6.14 (m, 1H), 6.25 (dd, J=10.1, 1.8 Hz, 1H), 7.07 (d, J=10.1 Hz, 1H)

Reference Example 2

(7α,20S)-7,21-Dihydroxy-20-methyl-pregna-1,4-dien-3-one (18.8 g) obtained by the procedure of Reference Example 1 was dissolved in 200 ml of methylene chloride, then 22 ml of pyridine and 0.5 g of dimethylaminopyridine were added, and the mixture was stirred for 30 minutes under ice cooling. To this solution was added 17.5 g of p-toluenesulfonyl chloride in several portions, and the mixture was further stirred at room temperature for 12 hours. The reaction mixture was poured into 65 ml of ice water and extracted with ethyl acetate (25 ml×2). The extracts were combined, washed in sequence with cooled 1N aqueous hydrochloric acid, a saturated aqueous solution of sodium hydrogen carbonate and a saturated aqueous solution of sodium chloride, dried over anhydrous sodium sulfate and concentrated under reduced pressure. The thus-obtained crude product was purified by silica gel chromatography to give 24.8 g of (7α,20S)-7-hydroxy-3-oxo-pregna-1,4-diene-20-methanol 4-methylbenzenesulfonate (compound of formula (I)) (yield 91%).

$^1$H-NMR spectrum (270 MHz, CDCl$_3$, TMS, ppm) δ: 0.71 (s, 3H), 0.99 (d, J=5.9 Hz, 3H), 1.22 (s, 3H), 2.45 (s, 3H), 2.45–2.50 (dd, J=13.9, 3.0 Hz, 1H), 2.73 (br dd, J=13.9, 2.0 Hz, 1H), 3.76 (dd, J=9.4, 6.4 Hz, 1H), 3.96–4.02 (dd, J=9.4, 4.0 Hz, 1H), 3.99–4.02 (m, 1H), 6.13 (br s, 1H), 6.24 (dd, J=9.9, 2.0 Hz, 1H), 7.05 (d, J=9.9 Hz, 1H), 7.35 (d, J=7.9 Hz, 2H), 7.77 (d, J=7.9 Hz, 2H)

EXAMPLE 1

(7α,20S)-7-Hydroxy-3-oxo-pregna-1,4-diene-20-methanol 4-methylbenzenesulfonate (60.0 g) obtained by the procedure of Reference Example 2 was dissolved in 1,000 ml of acetone, then 60.1 g of sodium iodide was added, and the mixture was heated under reflux for 3 hours. The reaction mixture was filtered, and the filtrate was concentrated under reduced pressure. The crude product obtained was purified by silica gel chromatography to give 42.1 g of (7α,20S)-7-hydroxy-21-iodo-20-methyl-pregna-1,4-dien-3-one (compound of general formula (II)) (yield 92.5%).

$^1$H-NMR spectrum (270 MHz, CDCl$_3$, TMS, ppm) δ: 0.78 (s, 3H), 1.03 (d, J=5.4 Hz, 3H), 1.24 (s, 3H), 2.49 (dd, J=13.9, 3.0 Hz, 1H), 2.73 (ddd, J=13.9, 3.0, 2.0 Hz, 1H), 3.16 (dd, J=9.7, 5.0 Hz, 1H), 3.33 (dd, J=9.7, 2.0 Hz, 1H), 4.03 (ddd, J=8.6, 3.0, 3.0 Hz, 1H), 6.15 (dd, J=2.0. 2.0 Hz, 1H), 6.26 (dd, J=10.4, 2.0 Hz, 1H), 7.06 (d, J=10.4 Hz, 1H)

EXAMPLE 2

Toluene (500 ml) was added to 20 ml of a 50% aqueous solution of sodium hydroxide, the water was removed by heating at 105–110° C. for 3 hours, the mixture was then cooled, 42.1 g of (7α,20S)-7-hydroxy-21-iodo-20-methyl-pregna-1,4-dien-3-one obtained by the procedure of Example 1 was added, 800 ml of toluene was further added, the mixture was again heated to 110° C., and the reaction was allowed to proceed for 8 hours while the byproduct water was distilled off by azeotropic distillation. The reaction mixture was cooled to room temperature, the residual sodium hydroxide was filtered off, and the filtrate was concentrated under reduced pressure. The crude product obtained was purified by silica gel chromatography to give 7.2 g of (20S)-21-iodo-20-methyl-pregna-1,4,6-trien-3-one (compound of general formula (III)) (yield 92%).

$^1$H-NMR spectrum (270 MHz, CDCl$_3$, TMS, ppm) δ: 0.83 (s, 3H), 1.04 (d, J=5.9 Hz, 3H), 1.20 (s, 3H), 3.16 (dd, J=9.4, 4.9 Hz, 1H), 3.33 (dd, J=9.4, 1.7 Hz, 1H), 6.00 (br s, 1H), 6.00–6.05 (dd, J=9.9, 2.0 Hz, 1H), 6.23 (dd, J=9.4, 3.0 Hz, 1H), 6.25 (dd, J=10.4, 2.0 Hz, 1H), 7.06 (d, J=10.4 Hz, 1H)

EXAMPLE 3

(7α,20S)-7-Hydroxy-21-iodo-20-methyl-pregna-1,4-dien-3-one (2.0 g) obtained by the procedure of Example 1 was suspended in 25 ml of toluene, 83.7 mg of p-toluenesulfonic acid was added, the mixture was heated to 110° C., and the reaction was allowed to proceed for 12 hours while distilling off the byproduct water by azeotropic distillation with toluene. The reaction mixture was cooled to room temperature and then concentrated under reduced pressure. The crude product obtained was purified by silica gel chromatography to give 1.2 g of (20S)-21-iodo-20-methyl-pregna-1,4,6-trien-3-one (compound of general formula (III)) (yield 64%).

$^1$H-NMR spectrum (270 MHz, CDCl$_3$, TMS, ppm) δ: 0.83 (s, 3H), 1.04 (d, J=5.9 Hz, 3H), 1.20 (s, 3H), 3.16 (dd, J=9.4, 4.9 Hz, 1H), 3.33 (dd, J=9.4, 1.7 Hz, 1H), 6.00 (br s, 1H), 6.00–6.05 (dd, J=9.9, 2.0 Hz, 1H), 6.23 (dd, J=9.4, 3.0 Hz, 1H), 6.25 (dd, J=10.4, 2.0 Hz, 1H), 7.06 (d, J=10.4 Hz, 1H)

EXAMPLE 4

(20S)-21-Iodo-20-methyl-pregna-1,4,6-trien-3-one (25.0 g) obtained by the procedure of Example 2 was suspended in 400 ml of isopropenyl acetate and 400 ml of butyl acetate, 39.5 g of p-toluenesulfonic acid was then added, and the mixture was heated to 105–115° C. and stirred for 8 hours. The reaction mixture was poured into 600 ml of a saturated aqueous solution of sodium hydrogen carbonate and extracted with 500 ml of ethyl acetate. The extract was washed in sequence with a saturated aqueous solution of sodium hydrogen carbonate and a saturated aqueous solution of sodium chloride, then dried over anhydrous sodium sulfate and concentrated under reduced pressure to give 34.4 g of (20S)-21-iodo-20-methyl-pregna-1,3,5,7-tetraen-3-ol acetate (compound of general formula (IV)) (purity determined by high performance liquid chromatography (HPLC): 92% (area ratio)).

$^1$H-NMR spectrum (270 MHz, CDCl$_3$, TMS, ppm) δ: 0.69 (s, 3H), 0.79 (s, 3H), 1.08 (d, J=5.9 Hz, 3H), 2.19 (s, 3H), 3.20 (dd, J=9.4, 5.4 Hz, 1H), 3.35 (dd, J=9.4, 2.5 Hz, 1H), 5.70 (m, 1H), 5.90 (dd, J 9.9, 2.0 Hz, 1H), 5.97–6.03 (m, 3H)

EXAMPLE 5

(20S)-21-Iodo-20-methyl-pregna-1,3,5,7-tetraen-3-ol acetate (3.45 g) obtained by the procedure of Example 4 (purity determined by HPLC: 92% (area ratio)) was dissolved in 200 ml of tetrahydrofuran, and 200 ml of ethanol was added. To this solution was added a solution of calcium borohydride in tetrahydrofuran (about 1 M, 143.3 ml) in several portions at 0° C., and the resulting mixture was then stirred with ice cooling for 7 hours. The excess calcium borohydride was decomposed by adding 540 ml of a 10% aqueous solution of acetic acid to the reaction mixture, and then the mixture was extracted with 900 ml of ethyl acetate. The extract was washed in sequence with a saturated aqueous solution of sodium hydrogen carbonate and a saturated aqueous solution of sodium chloride, then dried over anhydrous sodium sulfate and concentrated under reduced pressure. The crude product obtained was purified by silica gel chromatography to give 14.8 g of (3β,20S)-21-iodo-20-methyl-pregna-1,5,7-trien-3-ol (compound of general formula (V-1)) (yield based on (20S)-21-iodo-20-methyl-pregna-1,4,6-trien-3-one: 59.0%).

$^1$H-NMR spectrum (270 MHz, CDCl$_3$, TMS, ppm) δ: 0.67 (s, 3H), 1.01 (s, 3H), 1.06 (d, J=5.9 Hz, 3H), 2.27 (dd, J=12.4, 10.4 Hz, 1H), 2.58 (ddd, J=12.4, 5.4, 1.5 Hz, 1H), 3.19 (dd, J=9.4, 5.4 Hz, 1H), 3.34 (dd, J=9.4, 2.5 Hz, 1H), 4.31 (m, 1H), 5.46 (m, 1H), 5.64 (d, J=10.4 Hz, 1H), 5.67 (m, 1H), 5.71 (dd, J=10.4, 2.0 Hz; 1H)

EXAMPLE 6

(3β,20S)-21-Iodo-20-methyl-pregna-1,5,7-trien-3-ol (14.8 g) obtained by the procedure of Example 5 was dissolved in 120 ml of methylene chloride, and 9.05 g of 2,6-lutidine was added. This solution was ice-cooled, 10.1 ml of tert-butyldimethylsilyl trifluoromethanesulfonate was added, and the mixture was then allowed to warm to room temperature and stirred for 1 hour. The reaction mixture was poured into 120 ml of a saturated aqueous solution of sodium hydrogen carbonate and extracted with 30 ml of methylene chloride. The extract was washed in sequence with 1 N hydrochloric acid, a saturated aqueous solution of sodium hydrogen carbonate and a saturated aqueous solution of sodium chloride, then dried over anhydrous sodium sulfate and concentrated under reduced pressure. The crude product obtained was purified by silica gel chromatography to give 18.05 g of (3β,20S)-3-tert-butyldimethylsilyloxy-21-iodo-20-methyl-pregna-1,5,7-triene (compound of general formula (V-2)) (yield 96.7%).

$^1$H-NMR spectrum (270 MHz, CDCl$_3$, ppm) δ: 0.089 (s, 6H), 0.66 (s, 3H), 0.91 (s, 9H), 0.99 (s, 3H), 1.06 (d, J=5.9 Hz, 3H), 2.34 (dd, J=12.4, 10.4 Hz, 1H), 2.42 (dd, J=12.4, 5.4 Hz, 1H), 3.19 (dd, J=9.4, 5.0 Hz, 1H), 3.34 (dd, J 9.4, 2.0 Hz, 1H), 4.31 (m, 1H), 5.46 (m, 1H), 5.57 (d, J=10.4 Hz, 1H), 5.64 (dd, J=10.4, 2.0 Hz, 1H), 5.68 (m, 1H)

EXAMPLE 7

In a nitrogen atmosphere, 5 ml of tetrahydrofuran and 0.1 ml of dibromoethylene were added to 3.4 g of metallic magnesium, the mixture was ice-cooled, and 30.0 g of 2,5,5-trimethyl-2-(2-bromoethyl)-1,3-dioxane and 75 ml of tetrahydrofuran were added dropwise to that mixture simultaneously over 1.5 hours. After completion of the dropping, the mixture was stirred for 1 hour with ice cooling and further at room temperature for 30 minutes to give bromo[2-(2,5,5-trimethyl-1,3-dioxan-2-yl)ethyl]magnesium (1.16 mol/l, tetrahydrofuran solution).

Then, in a nitrogen atmosphere, 74.4 mg of cuprous bromide-dimethyl sulfide complex was suspended in 2 ml of tetrahydrofuran, the suspension was cooled to 0° C. and, to this suspension, there was added dropwise 7.8 ml of the solution of bromo[2-(2,5,5-trimethyl-1,3-dioxan-2-yl)ethyl]magnesium in tetrahydrofuran as prepared in the above manner. Thereafter, to this solution was added dropwise a solution of 1.0 g of (3β,20S)-3-tert-butyldimethylsilyloxy-21-iodo-20-methyl-pregna-1,5,7-triene obtained by the procedure of Example 6 in 10 ml of tetrahydrofuran, and the resulting mixture was stirred for 2 hours with ice cooling. The reaction mixture was poured into 30 ml of a saturated aqueous solution of ammonium chloride, 10 ml of water was added to thereby dissolve the insoluble matter, and the mixture was extracted with 10 ml of ethyl acetate. The extract was washed in sequence with a saturated aqueous solution of ammonium chloride and a saturated aqueous solution of sodium chloride, then dried over anhydrous sodium sulfate and concentrated under reduced pressure. The thus-obtained crude product was purified by silica gel chromatography to give 1.016 g of (3β,20S)-3-tert-butyldimethylsilyloxy-27-norcholesta-1,5,7-trien-25-one 2,2-dimethyl-1,3-propanediyl acetal (compound of general formula (VII)) (yield 96.3%).

$^1$H-NMR spectrum (270 MHz, CDCl$_3$, ppm) δ: 0.089 (s, 6H), 0.62 (s, 3H), 0.90 (s, 3H), 0.91 (s, 9H), 0.96 (d, J=6.4 Hz, 3H), 0.99 (s, 3H), 1.02 (s, 3H), 1.36 (s, 3H), 2.34 (dd, J=12.9, 10.9 Hz, 1H), 2.41 (dd, J=12.9, 5.9 Hz, 1H), 3.44 (d, J=11.4 Hz, 2H), 3.54 (d, J=11.4 Hz, 2H), 4.30 (m, 1H), 5.45 (m, 1H), 5.57 (d, J=10.4 Hz, 1H), 5.65 (dd, J=10.4, 2.0 Hz, 1H), 5.66 (m, 1H)

EXAMPLE 8

In a nitrogen atmosphere, 32.5 mg of cuprous bromide-dimethyl sulfide complex was suspended in 2 ml of tetrahydrofuran and, after cooling to 0° C., 4.8 ml of the solution of bromo[2-(2,5,5-trimethyl-1,3-dioxan-2-yl)ethyl] magnesium in tetrahydrofuran as prepared in the same manner as in Example 7 was added dropwise. Then, a solution of 0.4 g of (3β,20S)-21-bromo-3-tert-butyldimethylsilyloxy-20-methyl-pregna-1,5,7-triene in 4 ml of tetrahydrofuran was added dropwise, and the resulting mixture was stirred at room temperature for 2 days. The reaction mixture was poured into 20 ml of a saturated aqueous solution of ammonium chloride, 10 ml of water was added to thereby dissolve the insoluble matter, and the mixture was extracted with 20 ml of ethyl acetate. The extract was washed in sequence with a saturated aqueous solution of ammonium chloride and a saturated aqueous solution of sodium chloride, then dried over anhydrous sodium sulfate and concentrated under reduced pressure. The thus-obtained crude product was purified by silica gel chromatography to give 0.166 g of (3β,20S)-3-tert-butyldimethylsilyloxy-27-norcholesta-1,5,7-trien-25-one 2,2-dimethyl-1,3-propanediyl acetal (compound of general formula (VII)) (yield 36%).

$^1$H-NMR spectrum (270 MHz, CDCl$_3$, ppm) δ: 0.089 (s, 6H), 0.62 (s, 3H), 0.90 (s, 3H), 0.91 (s, 9H), 0.96 (d, J=6.4 Hz, 3H), 0.99 (s, 3H), 1.02 (s, 3H), 1.36 (s, 3H), 2.34 (dd, J=12.9, 10.9 Hz, 1H), 2.41 (dd, J=12.9, 5.9 Hz, 1H), 3.44 (d, J=11.4 Hz, 2H), 3.54 (d, J=11.4 Hz, 2H), 4.30 (m, 1H), 5.45 (m, 1H), 5.57 (d, J=10.4 Hz, 1H), 5.65 (dd, J=10.4, 2.0 Hz, 1H), 5.66 (m, 1H)

EXAMPLE 9

(3β,20S)-3-tert-Butyldimethylsilyloxy-27-norcholesta-1,5,7-trien-25-one 2,2-dimethyl-1,3-propanediyl acetal (490 mg) obtained by the procedure of Example 7 was dissolved in 10 ml of acetone and 5 ml of methylene chloride, 16.0 mg of p-toluenesulfonic acid monohydrate was added with ice cooling, and the mixture was stirred for 2 hours with ice cooling. One drop of triethylamine was added to the reaction mixture, and the mixture was concentrated under reduced pressure. The crude product thus obtained was purified by silica gel chromatography to give 381 mg of (3β,20S)-3-tert-butyldimethylsilyloxy-27-norcholesta-1,5,7-trien-25-one (compound of general formula (VIII)) (yield 91.2%).

$^1$H-NMR spectrum (270 MHz, CDCl$_3$, ppm) δ: 0.089 (s, 6H), 0.62 (s, 3H), 0.91 (s, 9H), 0.96 (d, J=6.4 Hz, 3H), 0.99 (s, 3H), 2.13 (s, 3H), 4.30 (m, 1H), 5.45 (m, 1H), 5.57 (d, J=10.4 Hz, 1H), 5.65 (dd, J=10.4, 1.5 Hz, 1H), 5.66 (m, 1H)

EXAMPLE 10

Methylmagnesium bromide (0.93 M tetrahydrofuran solution, 3.3 ml) was cooled to −50° C., and a solution of 381 mg of (3β,20S)-3-tert-butyldimethylsilyloxy-27-norcholesta-1,5,7-trien-25-one obtained by the procedure of Example 9 in 5 ml of tetrahydrofuran was added dropwise, and the resulting mixture was stirred at −50° C. for 2 hours. The reaction mixture was poured into a saturated aqueous solution of ammonium chloride and extracted with 10 ml of ethyl acetate. The extract was washed in sequence with a saturated aqueous solution of sodium hydrogen carbonate and a saturated aqueous solution of sodium chloride, then dried over anhydrous sodium sulfate and concentrated under reduced pressure. The crude product obtained was purified by silica gel chromatography to give 392 mg of (3β,20S)-3-tert-butyldimethylsilyloxy-cholesta-1,5,7-trien-25-ol (compound of general formula (IX)) (yield 99.7%).

$^1$H-NMR spectrum (270 MHz, CDCl$_3$, ppm) δ: 0.088 (d, J=1.5 Hz, 6H), 0.62 (s, 3H), 0.91 (s, 9H), 0.96 (d, J=6.4 Hz, 3H), 1.00 (s, 3H), 1.22 (s, 6H), 2.35 (dd, J=12.4, 10.4 Hz, 1H), 2.41 (dd, J=12.4, 5.4 Hz, 1H), 5.45 (m, 1H), 5.56 (d, J=9.9 Hz, 1H), 5.65 (dd, J=9.9. 2.0 Hz, 1H), 5.65 (m, 1H)

EXAMPLE 11

(3β,20S)-3-tert-Butyldimethylsilyloxy-cholesta-1,5,7-trien-25-ol (515 mg) obtained by the procedure of Example 10 was dissolved in 3 ml of methylene chloride, and a solution of 183.9 mg of 4-phenyl-1,2,4-triazolidine-3,5-dione in 5 ml of methylene chloride was added dropwise at room temperature. The mixture was then stirred for 1 hour. The reaction mixture was concentrated under reduced pressure and the crude product thus obtained was purified by silica gel chromatography to give 670 mg of (3β,20S)-3-tert-butyldimethylsilyloxy-5α,8α-(4-phenyl-3,5-dioxo-1,2,4-triazolidine-1,2-diyl)-cholesta-1,6-dien-25-ol (compound of general formula (X)) (yield 97.0%).

$^1$H-NMR spectrum (270 MHz, CDCl$_3$, ppm) δ: 0.093 (d, J=4.9 Hz, 6H), 0.82 (s, 3H), 0.89 (s, 9H), 0.95 (d, J=6.4 Hz, 3H), 1.10 (s, 3H), 1.21 (s, 6H), 2.31 (dd, J=14.8, 6.4 Hz, 1H), 2.39–2.50 (m, 2H). 3.32 (dd, J=14.8, 7.9 Hz, 1H), 4.97 (m, 1H), 5.66 (dd, J=9.9, 3.5 Hz, 1H), 5.70 (d, J=9.9 Hz, 1H), 6.26 (d, J=8.4 Hz, 1H), 6.45 (d, J=7.9 Hz, 1H), 7.28–7.41 (m, 5H)

INDUSTRIAL APPLICABILITY

The present invention provides steroid derivatives useful as intermediates for the production of vitamin D derivatives, such as 1α,25-dihydroxyvitamin D$_3$ or 2β-(3-hydroxypropoxy)-1α,25-dihydroxyvitamin D$_3$, as well as a process for producing the same.

The steroid derivatives provided by the present invention are useful as intermediates for the synthesis of vitamin D derivatives, such as 1α,25-dihydroxyvitamin D$_3$ and 2β-(3-hydroxypropoxy)-1α,25-dihydroxyvitamin D$_3$, which have calcium metabolism modulating activity and differentiation inducing activity and are effective as therapeutic agents for diseases caused by calcium metabolism disorder, such as osteoporosis and osteomalacia, or as antitumor agents.

What is claimed is:
1. A halide compound represented by the general formula (II):

(II)

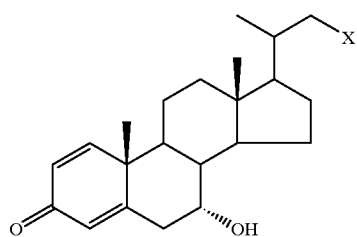

wherein X represents a bromine atom or an iodine atom.

2. A 1,4,6-trien-3-one compound represented by the general formula (III):

(III)

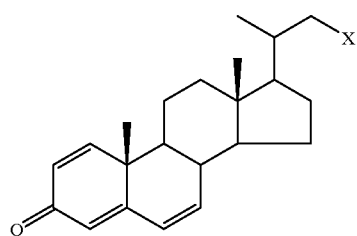

wherein X represents a bromine atom or an iodine atom.

3. A 1,3,5,7-tetraene compound represented by the general formula (IV):

(IV)

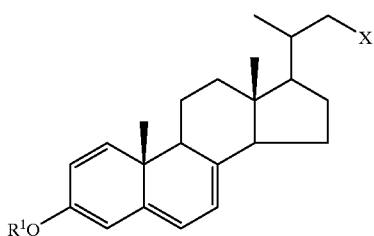

wherein X represents a bromine atom or an iodine atom and R¹ represents an acyl group.

4. A 1,5,7-triene compound represented by the general formula (V):

(V)

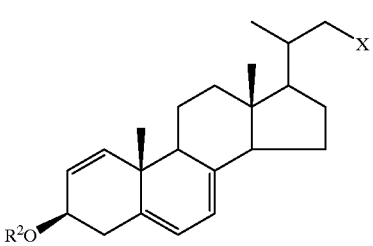

wherein X represents a bromine atom or an iodine atom and R² represents a hydrogen atom or a hydroxy-protecting group.

5. A process for producing 3β-hydroxy-1,5,7-triene compounds represented by the general formula (V-1):

(V-1)

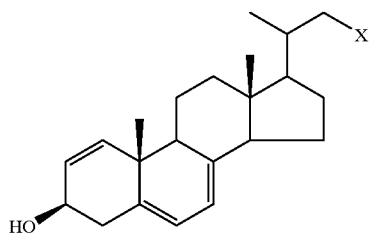

wherein X represents a bromine atom or an iodine atom, which comprises reducing a 1,3,5,7-tetraene compound represented by the general formula (IV):

(IV)

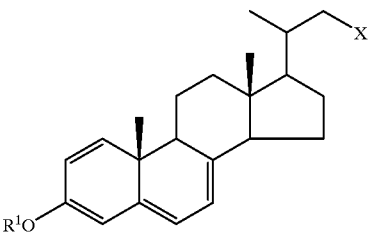

wherein X is as defined above and R¹ represents an acyl group.

6. A process for producing 1,3,5,7-tetraene compounds represented by the general formula (IV):

(IV)

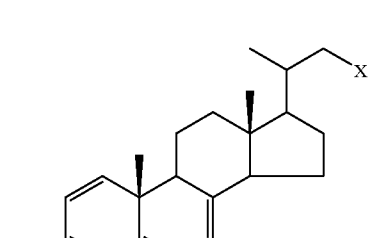

wherein X represents a bromine atom or an iodine atom and R¹ represents an acyl group, which comprises subjecting a 1,4,6-trien-3-one compound represented by the general formula (III):

(III)

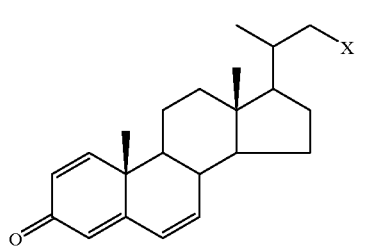

wherein X is as defined above, to enol esterification.

7. A process for producing 1,4,6-trien-3-one compounds represented by the general formula (III):

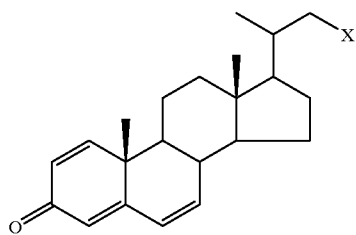

(III)

wherein X represents a bromine atom or an iodine atom, which comprises dehydrating the hydroxy group at position 7 of a halide compound represented by the general formula (II):

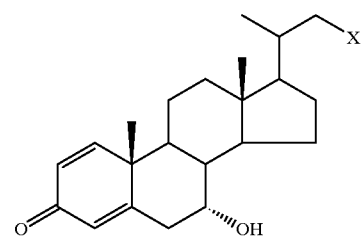

(II)

wherein X is as defined above.

8. A process for producing halide compounds represented by the general formula (II):

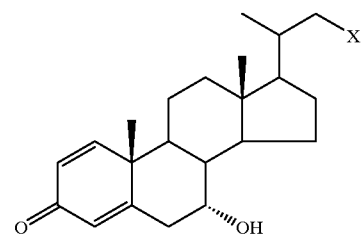

(II)

wherein X represents a bromine atom or an iodine atom, which comprises reacting a sulfonate compound represented by the general formula (I):

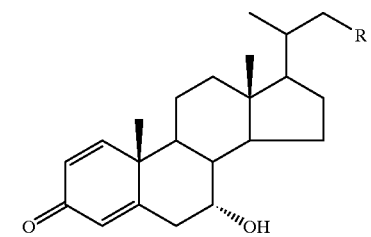

(I)

wherein R represents an organic sulfonyloxy group, with a brominating agent or an iodinating agent.

9. A process for producing diene adducts represented by the general formula (X):

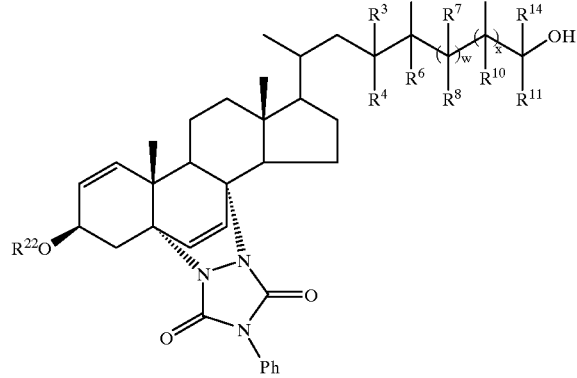

(X)

wherein $R^{22}$ represents a hydroxy-protecting group, $R^3$, $R^4$, $R^5$ and $R^6$ each represents a hydrogen atom or an alkyl group, $R^7$, $R^8$, $R^9$ and $R^{10}$ each represents a hydrogen atom, a fluorine atom, a protected hydroxy group or an alkyl group, $R^3$ and $R^5$, $R^4$ and $R^6$ or $R^5$ and $R^7$ may combinedly represent a single bond, $R^{11}$ represents a hydrogen atom, a trifluoromethyl group, a cycloalkyl group or an alkyl group which may optionally be substituted by a protected hydroxy group, $R^{14}$ represents an alkyl group, w represents 0 or 1 and x represents 0, 1, or 2, which comprises reacting a sulfonate compound represented by the general formula (I):

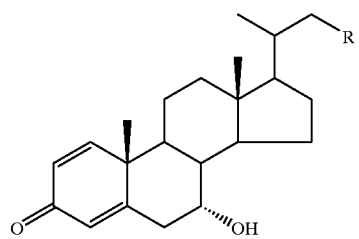

(I)

wherein R represents an organic sulfonyloxy group, with a brominating agent or an iodinating agent, to give a halide compound represented by the general formula (II):

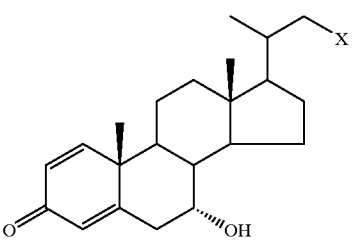

(II)

wherein X represents a bromine atom or an iodine atom, dehydrating the hydroxy group at position 7 of the thus-obtained halide compound to give a 1,4,6-trien-3-one compound represented by the general formula (III):

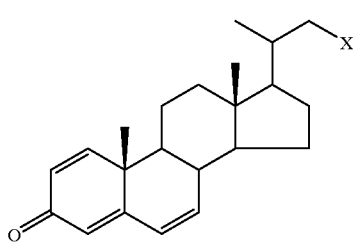

(III)

wherein X is as defined above, subjecting the thus-obtained 1,4,6-trien-3-one compound to enol esterification to give a 1,3,5,7-tetraene compound represented by the general formula (IV):

(IV)

wherein X is as defined above and $R^1$ represents an acyl group, reducing the thus-obtained 1,3,5,7-tetraene compound to give a 3β-hydroxy-1,5,7-triene compound represented by the general formula (V-1):

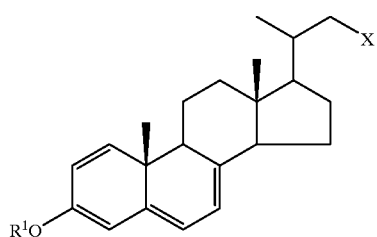

(V-1)

wherein X is as defined above, protecting the hydroxy group at position 3 of the thus-obtained 3β-hydroxy-1,5,7-triene compound to give a 1,5,7-triene compound represented by the general formula (V-2):

(V-2)

wherein X and $R^{22}$ are as defined above, reacting the thus-obtained 1,5,7-triene compound with an organometallic compound represented by the general formula (VI):

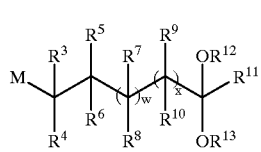

(VI)

wherein $R^3$, $R^4$, $R^5$, $R^6$, $R^7$, $R^8$, $R^9$, $R^{10}$, $R^{11}$, w and x are as defined above, $R^{12}$ and $R^{13}$ each independently represents an alkyl group or combinedly represent an alkylene group which may optionally be substituted by an alkyl group or groups and M represents Li or MgY (in which Y represents a halogen atom), in the presence of a copper compound to give an acetal compound represented by the general formula (VII):

(VII)

wherein $R^{22}$, $R^3$, $R^4$, $R^5$, $R^6$, $R^7$, $R^8$, $R^9$, $R^{10}$, $R^{11}$, $R^{12}$, $R^{13}$, w and x are as defined above, deprotecting the acetal moiety of the thus-obtained acetal compound to give a ketone compound represented by the general formula (VIII):

(VIII)

wherein $R^{22}$, $R^3$, $R^4$, $R^5$, $R^6$, $R^7$, $R^8$, $R^9$, $R^{10}$, $R^{11}$, w and x are as defined above, reacting the thus-obtained ketone compound with an alkylating agent to give a hydroxy compound represented by the general formula (IX):

(VIII)

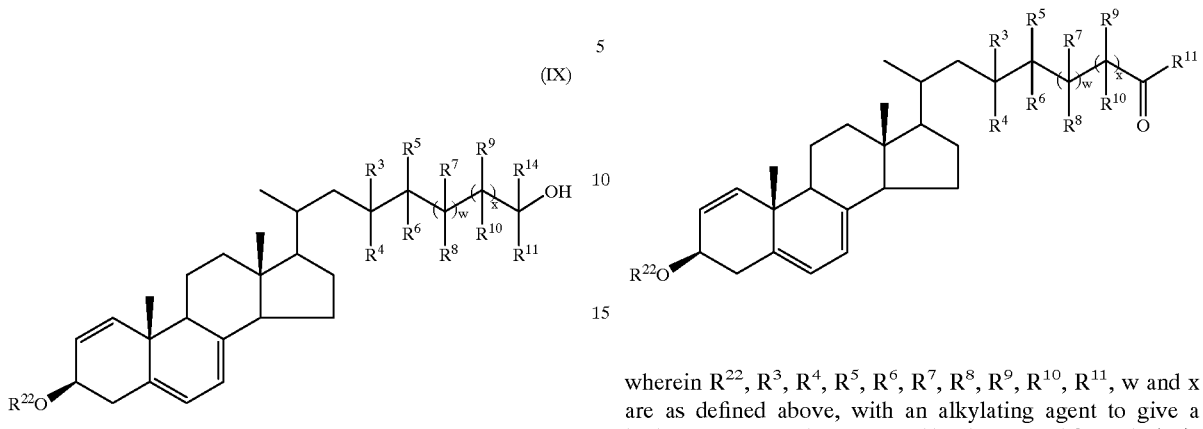

wherein $R^{22}$, $R^3$, $R^4$, $R^5$, $R^6$, $R^7$, $R^8$, $R^9$, $R^{10}$, $R^{11}$, w and x are as defined above, with an alkylating agent to give a hydroxy compound represented by the general formula (IX):

(IX)

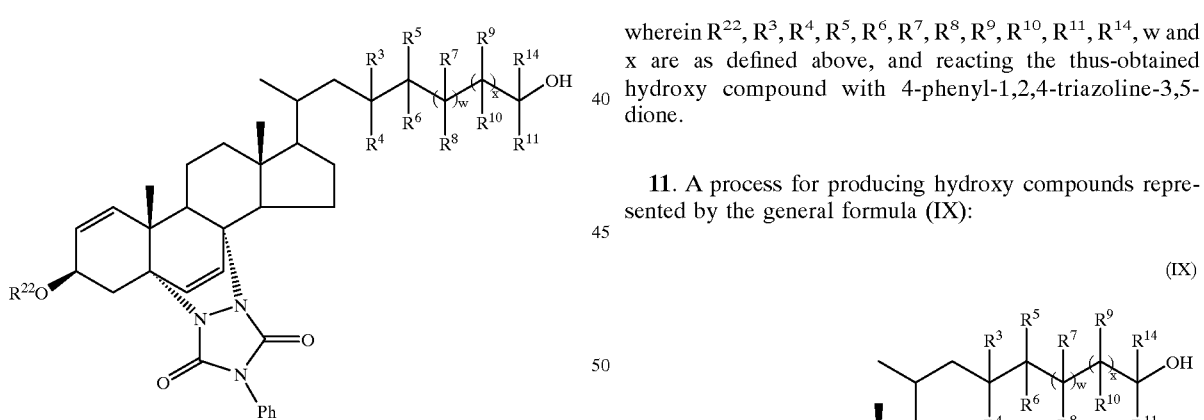

wherein $R^{22}$, $R^3$, $R^4$, $R^5$, $R^6$, $R^7$, $R^8$, $R^9$, $R^{10}$, $R^{11}$, $R^{14}$, w and x are as defined above, and reacting the thus-obtained hydroxy compound with 4-phenyl-1,2,4-triazoline-3,5-dione.

11. A process for producing hydroxy compounds represented by the general formula (IX):

(IX)

wherein $R^{22}$ represents a hydroxy-protecting group, $R^3$, $R^4$, $R^5$ and $R^6$ each represents a hydrogen atom or an alkyl group, $R^7$, $R^8$, $R^9$ and $R^{10}$ each represents a hydrogen atom, a fluorine atom, a protected hydroxy group or an alkyl group, $R^3$ and $R^5$, $R^4$ and $R^6$ or $R^5$ and $R^7$ may combinedly represent a single bond, $R^{11}$ represents a hydrogen atom, a (IX)

wherein $R^{22}$, $R^3$, $R^4$, $R^5$, $R^6$, $R^7$, $R^8$, $R^9$, $R^{10}$, $R^{11}$, $R^{14}$, w and x are as defined above, and reacting the thus-obtained hydroxy compound with 4-phenyl-1,2,4-triazoline-3,5-dione.

10. A process for producing diene adducts represented by the general formula X):

(X)

wherein $R^{22}$ represents a hydroxy-protecting group, $R^3$, $R^4$, $R^5$ and $R^6$ each represents a hydrogen atom or an alkyl group, $R^7$, $R^8$, $R^9$ and $R^{10}$ each represents a hydrogen atom, a fluorine atom, a protected hydroxy group or an alkyl group, $R^3$ and $R^5$, $R^4$ and $R^6$ or $R^5$ and $R^7$ may combinedly represents a single bond, $R^{11}$ represents a hydrogen atom, a trifluoromethyl group, a cycloalkyl group or an alkyl group which may optionally be substituted by a protected hydroxy group, $R^{14}$ represents an alkyl group, w represents 0 or 1 and x represents 0, 1 or 2, which comprises reacting a ketone compound represented by the general formula (VIII):

trifluoromethyl group, a cycloalkyl group or an alkyl group which may optionally be substituted by a protected hydroxy group, $R^{14}$ represents an alkyl group, w represents 0 or 1 and x represents 0, 1 or 2, which comprises reacting a ketone compound represented by the general formula (VIII):

(VIII)

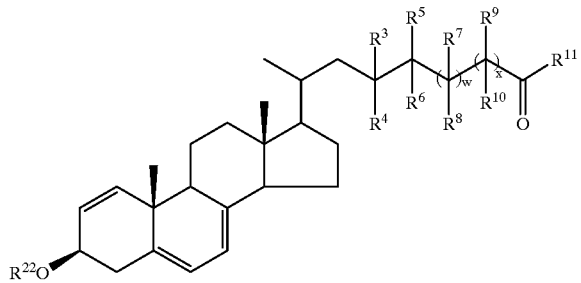

wherein $R^{22}$, $R^3$, $R^4$, $R^5$, $R^6$, $R^7$, $R^8$, $R^9$, $R^{10}$, $R^{11}$, w and x are as defined above, with an alkylating agent.

12. A process for producing ketone compounds represented by the general formula (VIII):

(VIII)

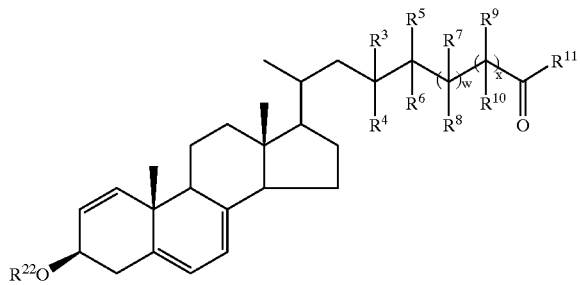

wherein $R^{22}$ represents a hydroxy-protecting group, $R^3$, $R^4$, $R^5$ and $R^6$ each represents a hydrogen atom or an alkyl group, $R^7$, $R^8$, $R^9$ and $R^{10}$ each represents a hydrogen atom, a fluorine atom, a protected hydroxy group or an alkyl group, $R^3$ and $R^5$, $R^4$ and $R^6$ or $R^5$ and $R^7$ may combinedly represent a single bond, $R^{11}$ represents a hydrogen atom, a trifluoromethyl group, a cycloalkyl group or an alkyl group which may optionally be substituted by a protected hydroxy group, w represents 0 or 1 and x represents 0, 1 or 2, which comprises reacting a 1,5,7-triene compound represented by the general formula (V-2):

(V-2)

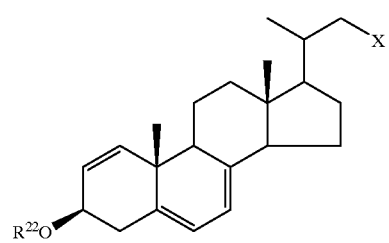

wherein X represents a bromine atom or an iodine atom and $R^{22}$ is as defined above, with an organometallic compound represented by the general formula (VI):

(VI)

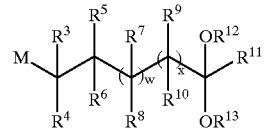

wherein $R^3$, $R^4$, $R^5$, $R^6$, $R^7$, $R^8$, $R^9$, $R^{10}$, $R^{11}$, w and x are as defined above, $R^{12}$ and $R^{13}$ each independently represents an alkyl group or combinedly represent an alkylene group which may optionally be substituted by an alkyl group or groups and M represents Li or MgY (in which Y represents a halogen atom), in the presence of a copper compound to give an acetal compound represented by the general formula (VII):

(VII)

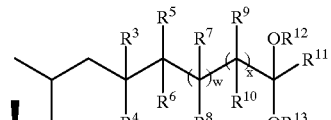

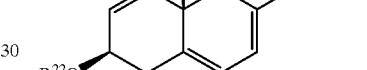

wherein $R^{22}$, $R^3$, $R^4$, $R^5$, $R^6$, $R^7$, $R^8$, $R^9$, $R^{10}$, $R^{11}$, $R^{12}$, $R^{13}$, w and x are as defined above, and deprotecting the acetal moiety of the thus-obtained acetal compound.

13. A process for producing acetal compounds represented by the general formula (VII):

(VII)

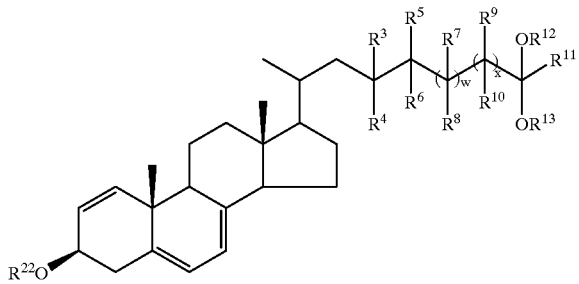

wherein $R^{22}$ represents a hydroxy-protecting group, $R^3$, $R^4$, $R^5$ and $R^6$ each represents a hydrogen atom or an alkyl group, $R^7$, $R^8$, $R^9$ and $R^{10}$ each represents a hydrogen atom, a fluorine atom, a protected hydroxy group or an alkyl group, $R^3$ and $R^5$, $R^4$ and $R^6$ or $R^5$ and $R^7$ may combinedly represent a single bond, $R^{11}$ represents a hydrogen atom, a trifluoromethyl group, a cycloalkyl group or an alkyl group which may optionally be substituted by a protected hydroxy group, $R^{12}$ and $R^{13}$ each independently represents an alkyl group or combinedly represent an alkylene group which may optionally be substituted by an alkyl group or groups, w represents 0 or 1 and x represents 0, 1 or 2, which comprises reacting a 1,5,7-triene compound represented by the general formula (V-2):

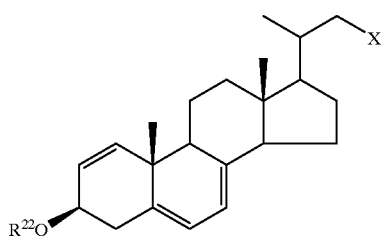

(V-2)

wherein X represents a bromine atom or an iodine atom and $R^{22}$ is as defined above, with an organometallic compound represented by the general formula (VI):

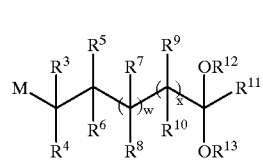

(VI)

wherein $R^3, R^4, R^5, R^6, R^7, R^8, R^9, R^{10}, R^{11}, R^{12}, R^{13}$, w and x are as defined above and M represents Li or MgY (in which Y represents a halogen atom), in the presence of a copper compound.

14. A process for producing 1,5,7-triene compounds represented by the general formula (V-2):

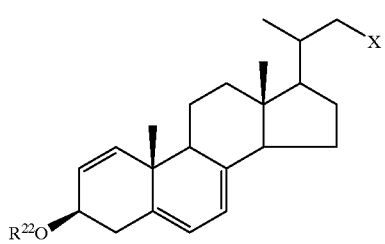

(V-2)

wherein X represents a bromine atom or an iodine atom and $R^{22}$ represents a hydroxy-protecting group, which comprises reacting a sulfonate compound represented by the general formula (I):

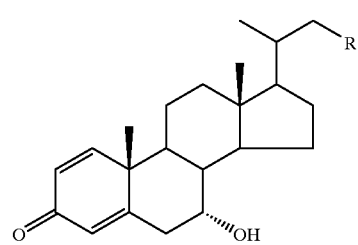

(I)

wherein R represents an organic sulfonyloxy group, with a brominating agent or an iodinating agent to give a halide compound represented by the general formula (II):

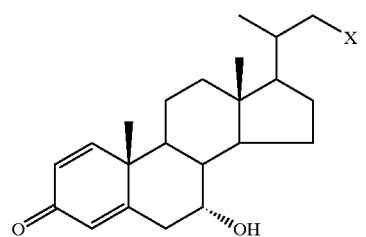

(II)

wherein X is as defined above, dehydrating the hydroxy group at position 7 of the thus-obtained halide compound to give a 1,4,6-trien-3-one compound represented by the general formula (III):

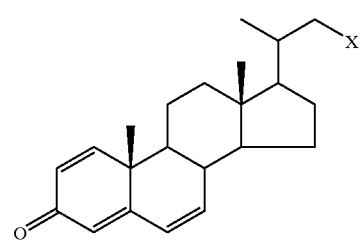

(III)

wherein X is as defined above, subjecting the thus-obtained 1,4,6-trien-3-one compound to enol esterification to give a 1,3,5,7-tetraene compound represented by the general formula (IV):

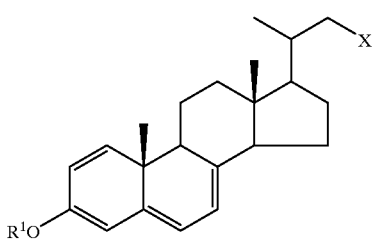

(IV)

wherein X is as defined above and $R^1$ represents an acyl group, reducing the thus-obtained 1,3,5,7-tetraene compound to give a 3β-hydroxy-1,5,7-triene compound represented by the general formula (V-1):

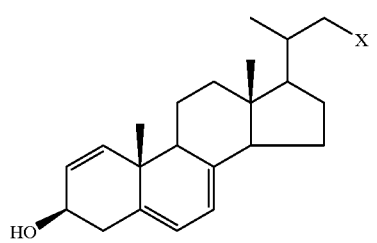

(V-1)

wherein X is as defined above, and protecting the hydroxy group at position 3 of the thus-obtained 3β-hydroxy-1,5,7-triene compound.

* * * * *